US010684341B2

(12) United States Patent
Helle et al.

(10) Patent No.: US 10,684,341 B2
(45) Date of Patent: Jun. 16, 2020

(54) MAGNETIC RESONANCE IMAGING OF ARTERIAL STRUCTURES

(71) Applicant: KONINKLIJKE PHILIPS N.V., Eindhoven (NL)

(72) Inventors: Michael Gunter Helle, Hamburg (DE); Thomas Lindner, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/094,907

(22) PCT Filed: Apr. 18, 2017

(86) PCT No.: PCT/EP2017/059101
§ 371 (c)(1),
(2) Date: Oct. 19, 2018

(87) PCT Pub. No.: WO2017/182424
PCT Pub. Date: Oct. 26, 2017

(65) Prior Publication Data
US 2019/0094326 A1    Mar. 28, 2019

(30) Foreign Application Priority Data
Apr. 21, 2016  (EP) ................................. 16166390

(51) Int. Cl.
*G01R 33/563* (2006.01)
*A61B 5/055* (2006.01)
*G01R 33/483* (2006.01)

(52) U.S. Cl.
CPC ........ *G01R 33/56316* (2013.01); *A61B 5/055* (2013.01); *G01R 33/4838* (2013.01); *G01R 33/5635* (2013.01); *G01R 33/56366* (2013.01)

(58) Field of Classification Search
CPC .......... G01R 33/56316; G01R 33/5635; A61B 5/055
(Continued)

(56) References Cited

U.S. PATENT DOCUMENTS 6,192,264 B1    2/2001  Foo et al.
9,523,753 B2 * 12/2016  Wang ................. G01R 33/5635
(Continued)

FOREIGN PATENT DOCUMENTS

WO    2015158879 A1    10/2015

OTHER PUBLICATIONS

Bernstein et al "Handbook of MRI Pulse Sequences" (2004) pp. 802-829.
(Continued)

*Primary Examiner* — Reena Aurora

(57) ABSTRACT

A method of magnetic resonance imaging (100, 200) includes acquiring (300) tagged magnetic resonance data (144) by controlling the magnetic resonance imaging system with tagging pulse sequence commands (140). The tagging pulse sequence commands include a tagging inversion pulse portion (404) for spin labeling a tagging location (122, 122') within a subject (118). The tagging pulse sequence commands comprise a phase-contrast readout portion (406) which phase-contrast encodes in at least one direction. The control pulse sequence commands include a control inversion pulse portion (500) and the phase-contrast readout portion. A tagged magnitude image (148) is reconstructed (304) using the tagged magnetic resonance data. A control magnitude image (150) is reconstructed (306) using the control magnetic resonance data. An arterial image (152) is reconstructed (308) by subtracting the control magnitude image and the tagged magnitude image. At least one phase image (156, 158, 160) is reconstructed (312) using either the
(Continued)

tagged magnetic resonance data and/or the control magnetic resonance data.

20 Claims, 9 Drawing Sheets

(58) Field of Classification Search
USPC .......................................................... 324/309
See application file for complete search history.

(56) References Cited

U.S. PATENT DOCUMENTS

| | | | |
|---|---|---|---|
| 2009/0129649 | A1 | 5/2009 | Djeridane |
| 2009/0143666 | A1 | 6/2009 | Edelman et al. |
| 2012/0139537 | A1 | 6/2012 | Holland et al. |
| 2012/0271157 | A1 | 10/2012 | Wong et al. |
| 2013/0034287 | A1 | 2/2013 | Itagaki et al. |
| 2013/0293231 | A1 | 11/2013 | Hirai |
| 2015/0305645 | A1* | 10/2015 | Ouyang ................ A61B 5/055 600/419 |
| 2015/0327783 | A1 | 11/2015 | Wang et al. |
| 2017/0219672 | A1* | 8/2017 | Miyazaki ........... G01R 33/4816 |

OTHER PUBLICATIONS

O'Gorman et al "In Vivo Estimation of the Flow-Driven Abiabatic Inversion Efficiency for Continuous Arterial Spin Labeling: A Method Using Phase Contrast Magnetic Resonance Agiography" Magnetic Reson. in Med. 55 p. 1291-1297 (2006).

Wu et al "Intravascular Effect in Velocity Selective Arterial Spin Labeling: The Coice of Inflow Time and Cutoff Velocity" Neuroimage 32.1 (2006) p. 122-128.

Haacke, E. Mark, et al. "11.2 Continous Properties and Phase Imaging" In: Magnetic resonance imaging: physical principles and sequence design. vol. 82. New York:: Wiley-Liss, 1999, ISBN: 978-0471351283.

Jensen-Kondering, Ulf, et al. "Superselective pseudo-continuous arterial spin labeling angiography." European journal of radiology 84.9 (2015): 1758-1767, DOI: 10.1016/j.ejrad.2015.05.034.

Thomas Lindner et al: "Selective arterial spin labeling in conjunction with phase-contrast acquisition for the simultaneous visualization of morphology, flow (direction, an(d velocity of individual arteries in the cerebrovascular system", Magnetic Resonance in Medicine.,Oct. 2016 (Oct. 31, 2016).

Andrew N. Priest et al:"Non-contrast-enhanced vascular magnetic resonance imaging using flow-dependent preparation with subtraction",Magnetic Resonance in Medicine, vol. 67, No. 3, Mar. 1, 2012 (Mar. 1, 2012), pp. 628-637.

Feng Xu et al: "Noninvasive quantification of whole-brain cerebral metabolic rate of oxygen (CMRO 2) by MRI", Magnetic Resonance in Medicine, vol. 62, No. 1, Jul. 1, 2009 (Jul. 1, 2009), pp. 141-148.

Hoad C et al: "Quantifying Blood Flow and Perfusion in Liver Tissue using Phase Contrast Angiography and Arterial Spin Labeling",Proceedings of the International Society for Magnetic Resonance in Medicine, ISMRM,19th Annual Meeting and Exhibition,Montreal, Quebec, May 7-13, 2011, Apr. 23, 2011 (Apr. 23, 2011), p. 794.

Michael Markl et al: "4D flow MRI", Journal of Magnetic Resonance Imaging, vol. 36, No. 5, Oct. 22, 2012 (Oct. 22, 2012), pp. 1015-1036.

Rodgers ZB et al: "Prospects for rapid CMRG2 quantification with interleaved TRUST, susceptometry-based oximetry, and phase-contrast MRI",Proceedings of the International Society or Magnetic Resonance in Medicine, ISMRM,Joint Annual Meeting ISMRM-ESMRMB, Milan, Italy, May 10-16, 2014,No. 751, Apr. 28, 2014 (Apr. 28, 2014), p. 751.

Ito K, et al. Noninvasive Evaluation of Collateral Blood Flow through Circle of Willis in Cervical Carotid Stenosis Using Selective Magnetic Resonance Angiography; J Stroke Cerebrovasc Dis. May-Jun. 2014;23(5):1019-23. doi: 10.1016/j.strokecerebrovasdis. 2013.08.018. Epub Oct. 6, 2013.

Lindner T Jensen-Kondering U, Wodarg F, Jansen O, Helle M. Non-Contrast Enhanced 4D Artery-Selective MR Angiography Using Spatially Selective Saturation. Proc Intl Soc Magn Reson Med. 2015.

Helle M, Norris DG, Rüfer S, Alfke K, Jansen O, van Osch MJ. Superselective pseudocontinuous arterial spin labeling. Magn Reson Med. Sep. 2010;64(3):777-86.

Alsop DC, Detre JA, Golay X, Günther M, Hendrikse J, Hernandez-Garcia L, Lu H, Macintosh BJ, Parkes LM, Smits M, van Osch MJ, Wang DJ, Wong EC, Zaharchuk G. Recommended implementation of arterial spin-labeled perfusion MRI for clinical applications: A consensus of the ISMRM perfusion study group and the European consortium for ASL in dementia. Magn Reson Med. Apr. 8, 2014. doi: 10.1002/mrm.25197. [Epub ahead of print].

Nakamura M, Yoneyama M, Tabuchi T, Takemura A, Obara M, Tatsuno S, Sawano S. Vessel-selective, non-contrast enhanced, time-resolved MR angiography with vessel-selective arterial spin labeling technique (CINEMA-SELECT) in intracranial arteries. Radiol Phys Technol. 2013;6:327-34.

Dumoulin CL, Souza SP, Walker MF, Wagle W. Three-dimensional phase contrast angiography. Magn Reson Med. Jan. 1989;9(1):139-49.

Willinek WA, Hadizadeh DR, von Falkenhausen M, Urbach H, Hoogeveen R, Schild HH, Gieseke J. 4D time-resolved MR angiography with keyhole (4D-TRAK): more than 60 times accelerated MRA using a combination of CENTRA, keyhole, and SENSE at 3.0T. J Magn Reson Imaging. Jun. 2008;27(6):1455-60.

Miyazaki M and Akahane M. Non-contrast enhanced MR angiography: established techniques. J Magn Reson Imaging. Jan. 2012;35(1):1-19.

Robson PM, Dai W, Shankaranarayanan A, Rofsky NM, Alsop DC. Time-resolved vessel-selective digital subtraction MR angiography of the cerebral vasculature with arterial spin labeling, Radiology 2010; 257:507-515.

Hartkamp et al "Mapping of Cerebral Perfusion Territories Using Territorial Arterial Spin Labeling Techniques and Clinical Application" NMR in Biology, Jul. 15, 2012.

* cited by examiner

MAGNETIC RESONANCE IMAGING OF ARTERIAL STRUCTURES

CROSS REFERENCE TO RELATED APPLICATIONS

This application is a U.S. national phase application of International Application No. PCT/EP2017/059101, filed on Apr. 18, 2017, which claims the benefit of EP Application Serial No. 16166390.1 filed on Apr. 21, 2016 and is incorporated herein by reference.

FIELD OF THE INVENTION

The invention relates to magnetic resonance imaging, in particular the invention is related to arterial spin tagging magnetic resonance imaging techniques.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by one or more transmitter coils cause a called B1 field. Additionally applied gradient fields and the B1 field cause perturbations to the effective local magnetic field. RF signals are then emitted by the nuclear spins and detected by one or more receiver coils. These RF signals are used to construct the MR images. These coils can also be referred to as antennas.

MRI scanners are able to construct images of either slices or volumes. A slice is a thin volume that is only one voxel thick. A voxel is a small volume element over which the MR signal is averaged, and represents the resolution of the MR image. A voxel may also be referred to as a pixel (picture element) herein if a single slice is considered.

By performing different magnetic resonance imaging protocols (which are implemented as pulse sequences or pulse sequence commands), different types of information can be measured about a subject. For example, there are various techniques, which enable the encoding of spins such that the flow or diffusion of fluid can be directly measured. Arterial spin tagging is a technique where the spins of blood passing through a group of arteries or even single arteries can be labeled and then imaged. The reference book "Handbook of MRI Pulse Sequences" (hereafter "Handbook of MRI Pulse Sequences") by Bersnstein et. al., Elsevier, 2004, ISBN 978-0-12-092861-3 describes in section 17.1 (pp. 802 through 829) provides a review of several different arterial spin tagging techniques.

The journal article "In Vivo Estimation of the Flow-Driven Adiabatic Inversion Efficiency for Continuous Arterial Spin Labeling: A Method Using Phase Contrast Magnetic Resonance Angiography," O'Gorman et. al., Magnetic Resonance in Medicine 55:1291-1297 (2006) describes the combination of arterial spin labeling with an estimation of the flow-driven adiabatic inversion efficiency. Axial velocity maps are acquired using a peripherally gated 2D triggered phase contrast sequence and are acquired separately from perfusion measurements using a multi-slice CASL technique.

Wu W C et al: "Intravascular effect in velocity selective arterial spin labeling: The choice of inflow time and cut off velocity", Neuroimage, Elsevier, Amsterdam NL, vol 32, no 1, 2006, pages 122-128) describe velocity selective arterial spin labeling on a basis of spin velocity instead of spatial distribution.

SUMMARY OF THE INVENTION

The invention provides for a magnetic resonance imaging system, a computer program product, and a method in the independent claims. Embodiments are given in the dependent claims.

Embodiments of the invention provide for an improved arterial spin tagging technique. The pulse sequences used for performing the arterial spin tagging technique incorporate a phase-contrast readout portion. Including a phase-contrast readout portion in the pulse sequences enables additional information to be acquired simultaneously with the spin tagging. The magnetic resonance data acquired may be processed in several ways to obtain this different information. Magnitude images can be reconstructed to locate arteries by detecting blood flow that has been tagged. The same magnetic resonance data may then be used to reconstruct phase images. The phase images may be used to detect the flow of fluid such as blood also.

Combining this phase information with the data from the magnitude images provides detailed information about the venous and arterial system. For example the magnitude images can be used to infer the location of tagged arteries directly. A knowledge of the location of the arteries from these tagged images can be used to create a mask which defines the location of known arteries. Flow information in the phase images which is within the location defined by the arteries can be attributed to flow within these arteries. Phase maps can then be used to determine the flow patterns of blood through arteries identified by the arterial mask.

Flow information within the phase images outside of the arterial masks can be attributed to flow within veins (or possibly untagged arteries). The phase maps can then be used to make a map of venous blood flow. It is even possible to make composite images which detail both arterial and venous blood flow.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect, the invention provides for a magnetic resonance imaging system for imaging a subject. The subject may for instance be at least partially within an imaging zone of the magnetic resonance imaging system. The magnetic resonance imaging system comprises a memory for storing machine-executable instructions. The memory further contains tagging pulse sequence commands and control pulse sequence commands. The tagging pulse sequence commands comprise a tagging inversion pulse portion for spin labeling a tagging location within the subject. The tagging pulse sequence commands further comprise a phase-contrast readout portion. The phase-contrast readout portion comprises a phase-contrast encoding in at least one direction. The control pulse sequence commands comprise a control inversion pulse portion. The control pulse sequence commands comprise the phase-contrast readout portion.

The tagging pulse sequence commands and the control pulse sequence commands are used for arterial spin tagging as is described in section 17.1 of the Handbook of MRI Pulse Sequences. The tagging inversion pulse portion is used to label a bolus of blood that is travelling through one or more arteries. The tagging inversion pulse portion results in a magnetization transfer effect that will be visible in a magnitude image calculated from magnetic resonance data that is acquired using the tagging pulse sequence commands. The control inversion pulse portion is constructed so that it causes a magnetization transfer effect that is equivalent or nearly equivalent to the magnetization transfer effect caused by the tagging inversion pulse portion.

The magnetic resonance imaging system further comprises a processor for controlling the magnetic resonance imaging system. Execution of the machine-executable instructions causes the processor to acquire tagged magnetic resonance data by controlling the magnetic resonance imaging system with the tagging pulse sequence commands. The tagged magnetic resonance data may for instance be acquired from a region of interest. Execution of the machine-executable instructions further cause the processor to acquire control magnetic resonance data by controlling the magnetic resonance imaging system with the control pulse sequence commands. The control magnetic resonance data may be acquired from the same region of interest as the tagged magnetic resonance data.

Execution of the machine-executable instructions further cause the processor to reconstruct a tagged magnitude image using the tagged magnetic resonance data. Execution of the machine-executable instructions further cause the processor to reconstruct a control magnitude image using the control magnetic resonance data.

Execution of the machine-executable instructions further cause the processor to reconstruct a using either the tagged magnetic resonance data and/or the control magnetic resonance data. The phase image is at least partially reconstructed using the phase encoding at least one direction. There may be a phase image reconstructed for each of the at least one direction.

In this embodiment the location of the arteries may be determined using the magnitude images and the location of veins are located using the phase images. The phase encoding is not affected by the tagging inversion pulse portion and the control inversion pulse portion. Therefore either the tagged magnetic resonance data and/or the control magnetic resonance data may be used to create the first, second and third phase images. In some instances it may be beneficial to use both the tagged magnetic resonance data and the control magnetic resonance data to increase the signal-to-noise ratio in the first phase image, the second phase image, and the third phase image.

In another embodiment, the at least one direction is a first direction, a second direction, and a third direction. The first direction, the second direction, and the third direction may be orthogonal. However, it is not necessary for the first direction, the second direction, and the third direction to be orthogonal. This embodiment may be beneficial because magnetic resonance imaging systems are normally fitted with three orthogonal magnetic field gradients. It may be efficient and produce good imaging results when the three directions are chosen to correspond to the orientation of the magnetic field gradient coils.

In another embodiment, execution of the machine-executable instructions further cause the processor to reconstruct a first phase image, a second phase image and a third phase image using either the tagged magnetic resonance data and/or the control magnetic resonance data. The first phase image is reconstructed using the phase encoding in the first direction. The second phase is reconstructed using the phase encoding in the second direction. The third phase image is reconstructed using the phase encoding in the third direction. The best results will be obtained when the first direction, the second direction and the third direction are orthogonal. However, the example described herein will still function when the first direction, the second direction, and the third direction are not orthogonal.

It may also be beneficial to use more than three directions. The phase contrast information from multiple images can be combined to improve the image quality.

In another embodiment execution of the machine executable instructions further causes the processor to construct a selective phase contrast arterial image at least partially by setting voxels of the phase image that are outside of the arterial mask to a predetermined background value. If there are multiple directions this may be performed for phase images reconstructed in each of the directions to create intermediate arterial phase contrast images.

In another embodiment Execution of the machine-executable instructions further cause the processor to construct an arterial image by subtracting the control magnitude image and the tagged magnitude image. Execution of the machine-executable instructions further cause the processor to construct an arterial mask using the arterial image by identifying arteries in the arterial image. The identification of the arteries may be performed in a number of different ways. The arterial image contains voxels with a larger value than the majority of the other voxels. These will most likely be portions of an artery. The location of arteries could therefore in one example be performed by thresholding the image. In other examples it may be possible to examine the connectedness of arteries. For example, it is expected that arteries would follow a path through which blood would flow. Voxels which are brighter than normal or above the threshold but are not connected to other voxels may in some instance be disregarded. In other examples anatomical models such as from an atlas or shape deformable models may be fit to the arterial image.

A mask as used herein encompasses a defined or identified region of an image or visualization of medical image data. For example, the arterial mask is constructed using the arterial image. The arterial mask is used to identify voxels or pixel within images that are identified as being part or partially composed of identified arteries. The arterial mask can then be applied or compared to other images and used to determine if the voxels in the other image contain identified arteries or not. If a voxel in an image is "within" or "inside" the arterial mask, then it contains an indentified artery or part of an identified artery. If a voxel is "outside" of the arterial mask then the voxel does not contain or partially contain an identified artery. Implicit in this is that there is known relationship between voxels of the image used to create the mask and the image to which the mask is being applied to. Normally, this is a one to one relationship between the voxels, however this is not necessary. When working with images produced by a single medical imaging system such as a single magnetic resonance imaging system the relationship or mapping between voxels in different images is well known.

In another embodiment execution of the machine executable instructions further causes the processor to construct a first intermediate arterial phase contrast image by setting voxels of the first phase image that are outside of the arterial mask to a predetermined background value. Execution of the machine executable instructions further cause the processor to construct a second intermediate arterial phase contrast image by setting voxels of the second phase image that are outside of the arterial mask to a predetermined background value. Execution of the machine executable instructions further cause the processor to construct a third intermediate arterial phase contrast image by setting voxels of the third phase image that are outside of the arterial mask to a predetermined background value. Execution of the machine executable instructions further cause the processor to calculate a selective phase contrast arterial image by adding the first intermediate arterial phase contrast image, the second intermediate arterial phase contrast image, the third intermediate arterial phase contrast image. This embodiment may have the advantage that a selective phase contrast arterial image is constructed where the flow and tagging information are acquired simultaneously. This may for example reduce the acquisition time. It may also reduce the amount of motion artifacts.

In another embodiment, execution of the machine-executable instructions further cause the processor to calculate a venous image at least partially by setting voxels within the venous image that correspond to or are within the arterial mask to the predetermined background value.

In another embodiment, execution of the machine-executable instructions further cause the processor to calculate a combined phase image by adding the first phase image, the second phase image, and the third phase image. Execution of the machine-executable instructions further cause the processor to calculate a venous image by setting all voxels within the combined phase image that are above a predetermined value and are also outside of the arterial mask. This may provide for a robust means of calculating the location of veins.

In another embodiment, the venous image is a selective phase contrast venous image. Execution of the machine executable instructions further cause the processor to construct a first intermediate venous phase contrast image by setting voxels of the first phase image that are outside of the arterial mask to a predetermined background value. Execution of the machine executable instructions further cause the processor to construct a second intermediate venous phase contrast image by setting voxels of the second phase image that are outside of the arterial mask to a predetermined background value. Execution of the machine executable instructions further cause the processor to construct a third intermediate venous phase contrast image by setting voxels of the third phase image that are outside of the arterial mask to a predetermined background value. Execution of the machine executable instructions further cause the processor to calculate the venous image by adding the first intermediate venous phase contrast image, the second intermediate venous phase contrast image, the third intermediate venous phase contrast image.

In the above embodiments, the tagging pulse sequence commands and the control pulse sequence commands are used to perform arterial spin tagging. The addition of the phase-contrast readout portion to both the tagging inversion pulse portion and the control inversion pulse portion enables the location of the veins to be determined using a single arterial spin tagging acquisition. The arteries are located in the magnitude images. This provides a knowledge of where the arteries are. This enables those particular voxels which belong to the arteries to then be excluded from the combined phase images. This may provide for an improved means of detecting the location of both arteries and veins within a subject.

In another embodiment the venous image and the arterial image are combined into a single image. In some examples false colors or other color scales may be used to indicate which are the venous and arterial portions of the image.

In another embodiment the venous image and the selective phase contrast arterial image are combined into a single image. In some examples false colors or other color scales may be used to indicate which are the venous and arterial portions of the image, and also the magnitude of flow through the arteries or veins.

In another embodiment the arterial image and the venous image are both three-dimensional images. In other examples they may be two-dimensional slabs or stacks of two-dimensional images. In other words the above embodiment may be performed as a two-dimensional, a series of two-dimensional acquisitions, or as a three-dimensional magnetic resonance imaging protocol.

In another embodiment the tagging volume is selectively positioned to encompass a cross-section of a single artery. The tagging volume may then be interpreted as selective labeling. This embodiment may be beneficial because the blood flow to the region of interest may be mapped for a single artery.

In another embodiment execution of the machine-executable instructions further cause the processor to repeat acquiring the tagged magnetic resonance data and the control magnetic resonance data for different tagging volumes. This for instance may be performed for a predetermined number of tagging volumes. Execution of the machine-executable instructions further causes the processor to calculate the arterial image for each of the predetermined number of tagging volumes. This embodiment may be useful in imaging a region which is supplied by more than one artery. For instance the brain is supplied by a number of different arteries. The blood supply for each of the individual arteries may be imaged separately.

When more than one artery is imaged, the arterial mask may be constructed using a composite of all the reconstructed arterial images for each of the different arteries. Likewise, the venous image may be reconstructed from the tagged magnetic resonance data and/or the control magnetic resonance data for one, all, or a combination of the magnetic resonance data acquired for the different arteries.

In another embodiment the tagging location is a tagging volume defined by one or more tagging voxels. In some examples this may be voxels identified in a preliminary magnetic resonance image which is used to determine the location of different arteries. Various voxels can be selected such that different arteries are selected.

In another embodiment the tagging location is non-selective. For example the tagging location may be a tagging plane. For example, when imaging the blood flow into the brain a plane may be selected which tags all of the arteries feeding the brain simultaneously. In this case the arterial image images the total blood supply to the brain and the venous image images the veins which are fed by these arteries.

In another embodiment execution of the machine-executable instructions further causes the processor to receive the tagging location. For example the processor may receive the tagging location via a user interface. In other cases the tagging location may be received automatically. For instance a preliminary medical image may provide or contain data which is descriptive of the location of arteries within a subject. An operator could manually delineate where the one or more tagging locations are within the subject. In other instances a system may perform this automatically.

In another embodiment the tagging location is received by segmenting a preliminary medical image. The preliminary medical image may be acquired using a different imaging modality such as a PET scan or a CT image. In other examples the preliminary medical image may be a scout scan or other image which is performed first with the subject already in location in the magnetic resonance imaging system. The segmentation algorithm may automatically identify the location of arteries or it may be simply used to position a tagging plane for non-selective tagging.

In another embodiment the venous image and the arterial image are both any one of the following: a planar image, a stack of planar images, and a three-dimensional image. That is to say the embodiment may be applied to a two-dimensional acquisition, a number of two-dimensional acquisitions or a full three-dimensional magnetic resonance imaging protocol.

In another embodiment execution of the machine-executable instructions cause the processor to calculate a composite image by combining the arterial image and the venous image into a composite image. The composite image may take different forms. In some examples different colors may be used to indicate the velocity of blood flow and/or whether it is arterial and/or venous. It may be beneficial to combine the arterial image and the venous image into one image as it may provide a better picture of the blood supply and drain from a region of interest. In particular, in imaging brain scans, it may help a practitioner to identify abnormal conditions in the subject more readily.

In another embodiment the multiple arterial images are acquired for different tagging volumes. These various arterial images may be combined also into a composite image which may be combined possibly with the venous image also. In a case where more than one tagging volume is used and they are selectively used to label different the arteries, the blood supply for different arteries may be labeled so it is easier to visualize the blood supply supplied by different arteries in relation to each other and also the vein system.

In another embodiment the arteries and the veins in the composite image are differentiated by color or different color scales.

In another embodiment the tagging pulse sequence commands comprise a pre-saturation portion before the tagging inversion pulse portion. The control pulse sequence commands comprise the pre-saturation portion before the control inversion pulse portion. The pre-saturation portion may be used to kill the magnetization of spins within a region of interest. Using the pre-saturation portion may provide better results when constructing the arterial image. It may provide for better signal-to-noise and also remove image artifacts. However, it is not necessary to perform the pre-saturation portion in the tagging pulse sequence commands and the control pulse sequence commands.

In another embodiment the arterial mask is created by thresholding the arterial image using a predetermined threshold value. Portions of the arterial image above the predetermined threshold value are identified as being arterial regions.

In another embodiment the arterial mask is at least partially created by segmenting the arterial image. A segmentation algorithm may be used to identify arteries within the arterial image. For instance an origin of the artery may be known and the segmentation algorithm may use the value of the pixel voxels in comparison with them being connected to each other.

In another embodiment the arterial mask is created at least partially by applying an anatomical atlas to the arterial image. For example the arteries within subjects with normal anatomy may be similar that anatomical atlases may be used to help identify which portions of the arterial image are arterial.

In another embodiment the arterial mask is at least partially created by fitting a deformable shape model to the arterial image. For example the deformable shape model may have a definition of a typical arterial system of a subject. This may be then deformed so that it fits within the arterial image.

In other embodiments the aforementioned methods of creating the arterial mask are combined or used separately and the results are combined to check and reduce the chance of air in creating the arterial mask.

In another embodiment execution of the tagging inversion pulse portion by the magnetic resonance imaging system causes a tagging magnetization transfer effect in the resultant tagged magnitude image. The control inversion pulse portion causes a control magnetization transfer effect in the control magnitude image. The tagging magnetization transfer effect is extracted out of the arterial image by the control magnetization transfer effect. When performing arterial spin tagging it is normal practice to perform a tagged image and a control image. The construction of the pulse sequences in this way enables a better image of the artery system to be performed. The use of tagging and non-tagging to create tagged images and control images is described in section 17.1 of the Handbook of MRI Pulse Sequences.

In another aspect the invention provides for a computer program product comprising instructions for execution by a processor controlling the magnetic resonance imaging system for imaging a subject. Execution of the machine-executable instructions causes the processor to acquire tagged magnetic resonance data by controlling the magnetic resonance imaging system with tagging pulse sequence commands. The tagging pulse sequence commands comprise a tagging inversion pulse portion for spin labeling a tagging location within the subject. The tagging pulse sequence commands comprise a phase-contrast readout portion. The phase-contrast readout portion comprises phase-contrast encoding in at least one direction. Execution of the machine-executable instructions further cause the processor to acquire control magnetic resonance data by controlling the magnetic resonance imaging system with the control pulse sequence commands. The control pulse sequence commands comprise a control inversion pulse portion. The control pulse sequence commands comprise the phase-contrast readout portion. Execution of the machine-executable instructions further cause the processor to reconstruct a tagged magnitude image using the tagged magnetic resonance data.

Execution of the machine-executable instructions further cause the processor to reconstruct a control magnitude image using the control magnetic resonance data. Execution of the machine-executable instructions further cause the processor to construct an arterial image by subtracting the tagged magnitude image from the control magnitude image. Execution of the machine-executable instructions further cause the processor to reconstruct a phase using either the tagged magnetic resonance data and/or the control magnetic resonance data. There may be a phase image is reconstructed for each of the at least one direction.

In another aspect, the invention provides for a method of operating the magnetic resonance imaging system for imaging a subject. The method comprises acquiring tagged magnetic resonance data by controlling the magnetic resonance imaging system with tagging pulse sequence commands. The tagging pulse sequence commands comprise a tagging inversion pulse portion for spin labeling a tagging location within the subject. The tagging pulse sequence commands comprise a phase-contrast readout portion. The phase-contrast readout portion comprises phase-contrast encoding in at least one direction.

The method further comprises acquiring control magnetic resonance data by controlling the magnetic resonance imaging system with the control pulse sequence commands. The control pulse sequence commands comprise a control inversion pulse portion. The control pulse sequence commands comprise the phase-contrast readout portion. The method further comprises reconstructing a tagged magnitude image using the tagged magnetic resonance data. The method further comprises reconstructing a control magnitude image using the control magnetic resonance data.

The method further comprises constructing an arterial image by subtracting the tagged magnitude image from the control magnitude image.

The method further comprises reconstructing a phase image using either the tagged magnetic resonance data and/or the control magnetic resonance data. The phase image may be for each of the at least one direction.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical image data. A Magnetic Resonance (MR) image is defined herein as being the reconstructed two or three dimensional visualization of anatomic data contained within the magnetic resonance imaging data. This visualization can be performed using a computer.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMB0DIMENTS

Like numbered elements in these figures are either equivalent elements or perform the same function. Elements which have been discussed previously will not necessarily be discussed in later figures if the function is equivalent.

Figure 1:
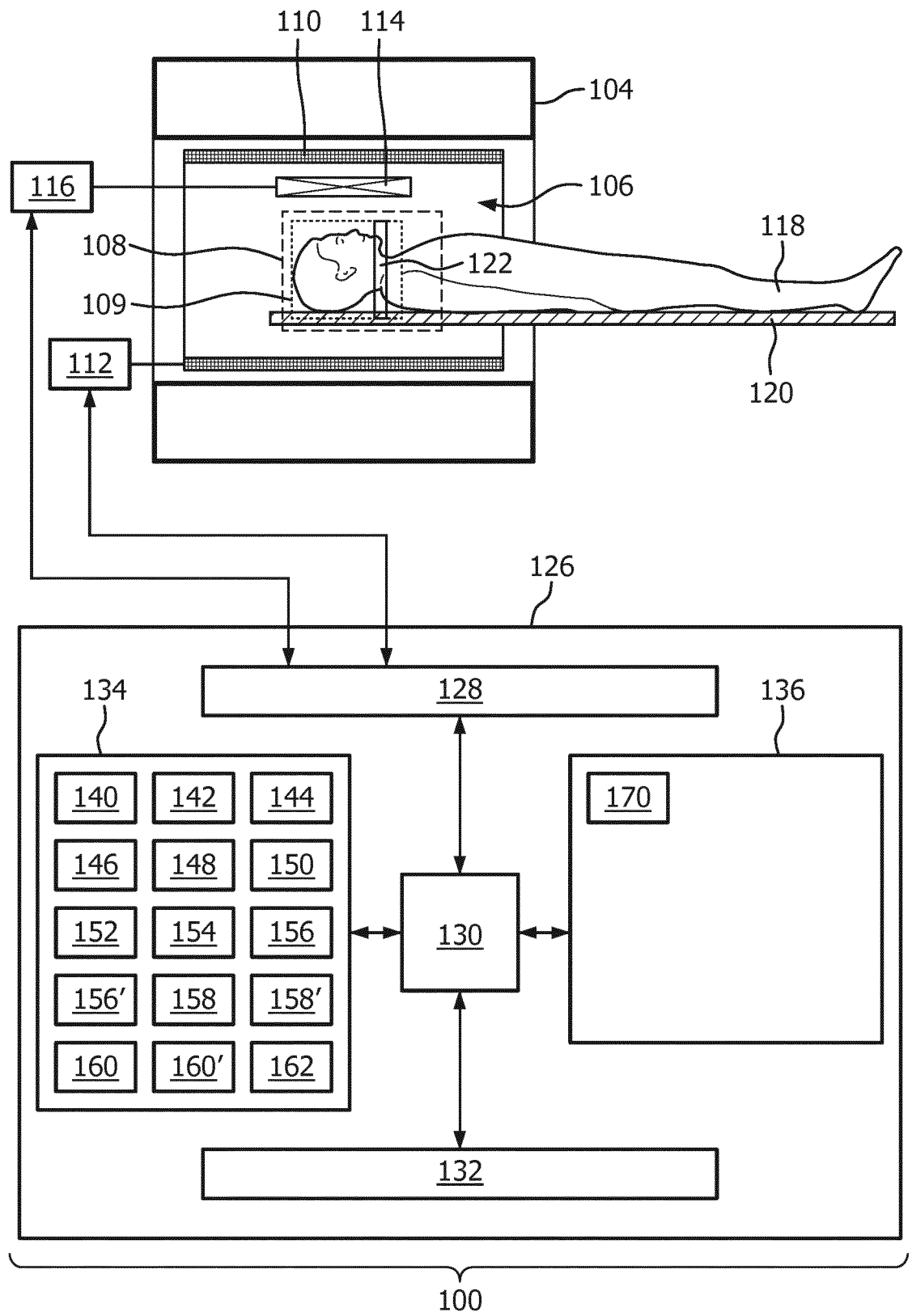
FIG. 1 illustrates an example of a magnetic resonance imaging system.

FIG. 1 shows an example of a magnetic resonance imaging system 100. The magnetic resonance imaging system 100 comprises a magnet 104. The magnet 104 is a superconducting cylindrical type magnet 104 with a bore 106 through it. The use of different types of magnets is also possible. Inside the cryostat of the cylindrical magnet, there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientation of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receiver. The radio-frequency coil 114 may also have multiple receive/transmit elements and the radio frequency transceiver 116 may have multiple receive/transmit channels.

Within the bore 106 of the magnet 104 there is a subject support 120 which supports the subject in the the imaging zone 108. A region of interest 109 can be seen within the imaging zone 108.

The transceiver 116, the magnetic field gradient coil power supply 112 are seen as being connected to a hardware interface 128 of computer system 126. The computer 126 further comprises a processor 130, a user interface 132, computer storage 134, and computer memory 136. The hardware interface 128 enables the processor 130 to send and receive commands and data in order to control the functioning of the magnetic resonance imaging system 100. The processor 130 is further connected to the user interface 132, the computer storage 134, and the computer memory 136.

The contents of the computer storage 134 and the computer memory 136 may be interchangeable. In some examples the contents of the computer storage 134 may be duplicated in the computer memory 136.

The computer storage 134 is shown as containing tagging pulse sequence commands 140. The computer storage 134 is further shown as containing control pulse sequence commands 142. The tagging pulse sequence commands 140 comprise a tagging inversion pulse portion for spin labeling the tagging location 122 within the subject 118. The tagging pulse sequence commands further comprise a phase-contrast readout portion. The phase-contrast readout portion comprises phase-contrast encoding in a first direction, a second direction, and a third direction. Normally these three directions would be aligned with the x, y and z-axis of the magnetic resonance magnet 104. This however is not necessary. The control pulse sequence commands comprise a control inversion pulse portion. The control pulse sequence commands 142 comprise the phase-contrast readout portion. The computer storage 134 is further shown as containing tagged magnetic resonance data 144 that has been acquired by controlling the magnetic resonance imaging system 100 using the tagging pulse sequence commands 140. The computer storage 134 is further shown as containing control magnetic resonance data 146 that has been acquired by controlling the magnetic resonance imaging system 100 with the control pulse sequence commands 142.

Pulse sequence commands as used herein encompass commands or a timing diagram which may be converted into commands which are used to control the functions of the magnetic resonance imaging system 100 as a function of time. Pulse sequence commands are the implementation of the magnetic resonance imaging protocol applied to a particular magnetic resonance imaging system 100.

Within the region of interest 109 there can be seen a tagging location 122. The tagging location is where the tagging inversion pulse portion labels a bolus of blood that passes through the arteries of the subject 118. In this case the region of interest 109 is shown as encompassing the head. The tagging location 122 in this case is a plane. The tagging is therefore non-selective and any blood passing through the plane 122 will be labeled. The positioning of the plane of the tagging location 122 near the neck of the subject 118 essentially means that all blood entering into the brain of the subject 118 will be effectively tagged. The example shown in FIG. 1 shows non-selective tagging.

The computer storage 134 further shows a tagged magnitude image 148 that has been reconstructed from the tagged magnetic resonance data. The computer storage 134 further shows a control magnitude image reconstructed from the control magnetic resonance data 146. When magnetic resonance data is acquired there may be different types of images which may be reconstructed. For example both magnitude and phase images may be reconstructed. In a normal clinical situation the magnitude image would indicate a density of hydrogen atoms at a particular location.

The computer storage 134 is further shown as containing an arterial image 152 that was constructed by subtracting the tagged magnitude image 150 from the controlmagnitude image 148. The computer storage 134 is further shown as containing an arterial mask 154. The arterial mask 154 is essentially an identification of the location of arteries within the arterial image 152. The arterial mask 154 can be constructed in different ways. A simple thresholding of the arterial image may be sufficient in some cases. In other examples more sophisticated methods such as a segmentation algorithm or fitting an anatomical atlas or model to the arterial image 154 may be used.

The computer storage 134 is further shown as containing a first phase image 156, a second phase image 154, and a third phase image 160. The first phase image 156, the second phase image 154, and the third phase image 160 may be reconstructed using the tagged magnetic resonance data 144 and/or the control magnetic resonance data 146 by using the phase encoding in the first, second, and third directions. The example illustrated in FIG. 1 is illustrative in that three encoding directions are used. In other examples there may be more or fewer encoding directions.

The computer storage 134 is further shown as containing a first intermediate arterial phase contrast image 156' that was calculated by setting voxels of the first phase image that are outside of the arterial mask to a predetermined background value. The computer storage 134 is shown as further containing a second intermediate arterial phase contrast image 158' which was calculated by setting voxels of the second phase image that are outside of the arterial mask to a predetermined background value. The computer storage 134 is further shown as containing a third intermediate arterial phase contrast image that was constructed or calculated by setting voxels of the third phase image that are outside of the arterial mask to a predetermined background value.

The computer storage is further shown as containing a selective phase contrast arterial image 162 that was calculated by adding the first intermediate arterial phase contrast image, the second intermediate arterial phase contrast image, the third intermediate arterial phase contrast image. If there are more or fewer phase encoding directions, there may be accordingly more or fewer selective phase contrast arterial images.

In other examples, the computer storage 134 may also contain a venous image 164. The venous image can created by applying the arterial mask 154 to the combined phase images 156, 158, 160 to exclude voxels that are identified as belonging to the arterial system of the subject 118. Remaining voxels above a predetermined threshold or value may then be interpreted as belonging to the vein system.

Figure 2:
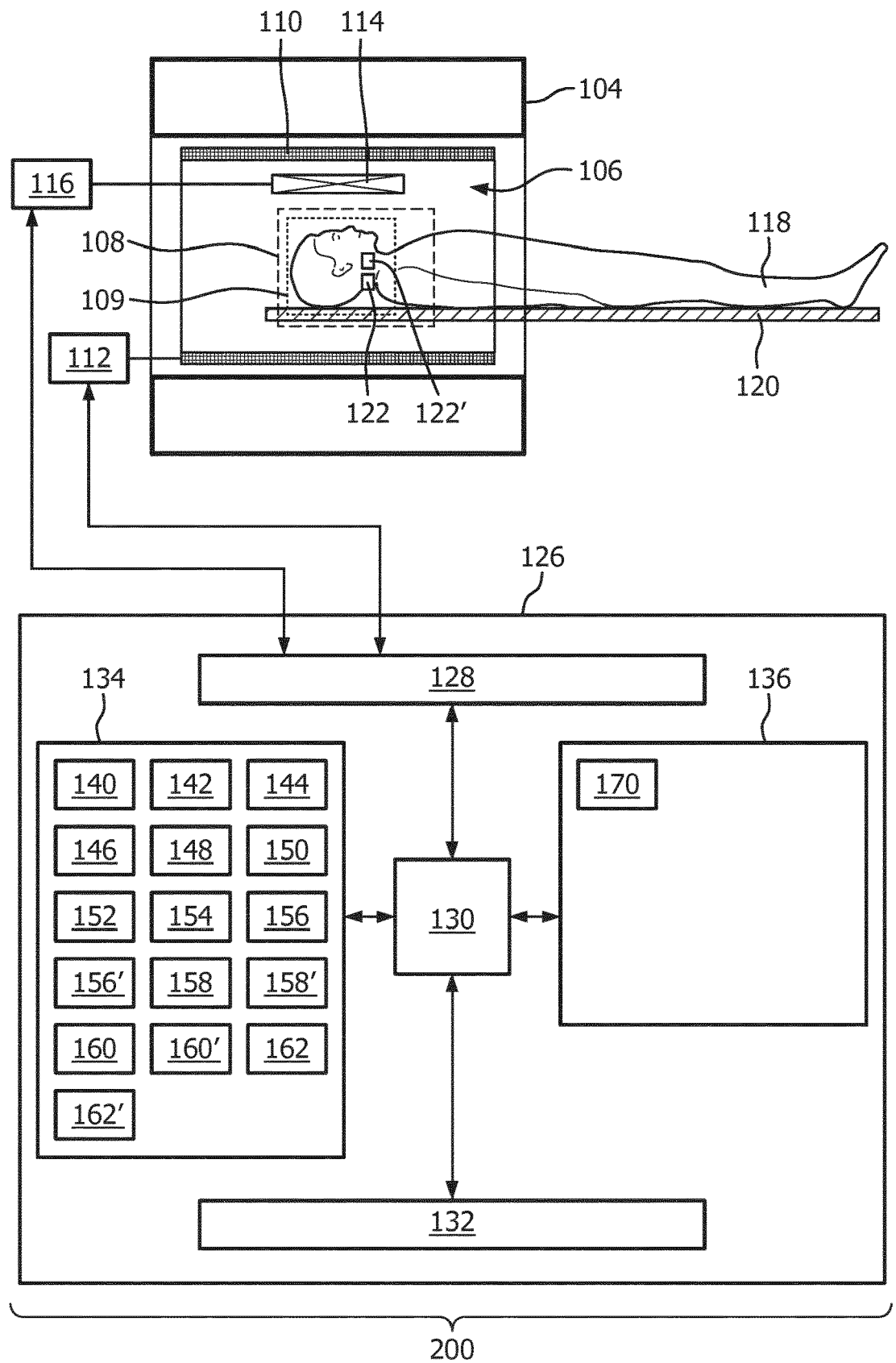
FIG. 2 illustrates a further example of a magnetic resonance imaging system.

The computer storage 134 is further shown as containing a composite image 166 which is created by combining the venous image 164 with either the arterial image 152 or the selective phase contrast arterial image. In some cases the composite image may also be created by combining the venous image 164 with the arterial mask 154. The composite image 166 may in some cases use different colors or other emphasizing marks to differentiate between arteries and veins within the image. FIG. 2 shows a further example of a magnetic resonance imaging system 200.

The magnetic resonance imaging system 200 is similar to the system 100 shown in FIG. 1. However in this example there is more than one tagging location. The two tagging locations 122, 122' may be positioned such that individual arteries are selectively tagged. This is an example of selective tagging. In this example the computer storage 134 is further shown as containing a selective phase contrast arterial image 162' corresponding to an acquisition made when the tagging location is 122'. Arterial images corresponding to the tagging locations 122, 122' can both be combined to make the arterial mask 154. In this way individual arteries can contribute to the arterial mask 154 and be subtracted from the venous image 164. The acquisition may be run an arbitrary number of times with different tagging locations 122, 122' so that a composite image 166 can be made comprising contributions from an arbitrary number of arteries. For example different arteries could be color coded or marked in different ways in the image so that the blood contribution from individual arteries can be mapped within a region of the subject 118.

Figure 3:
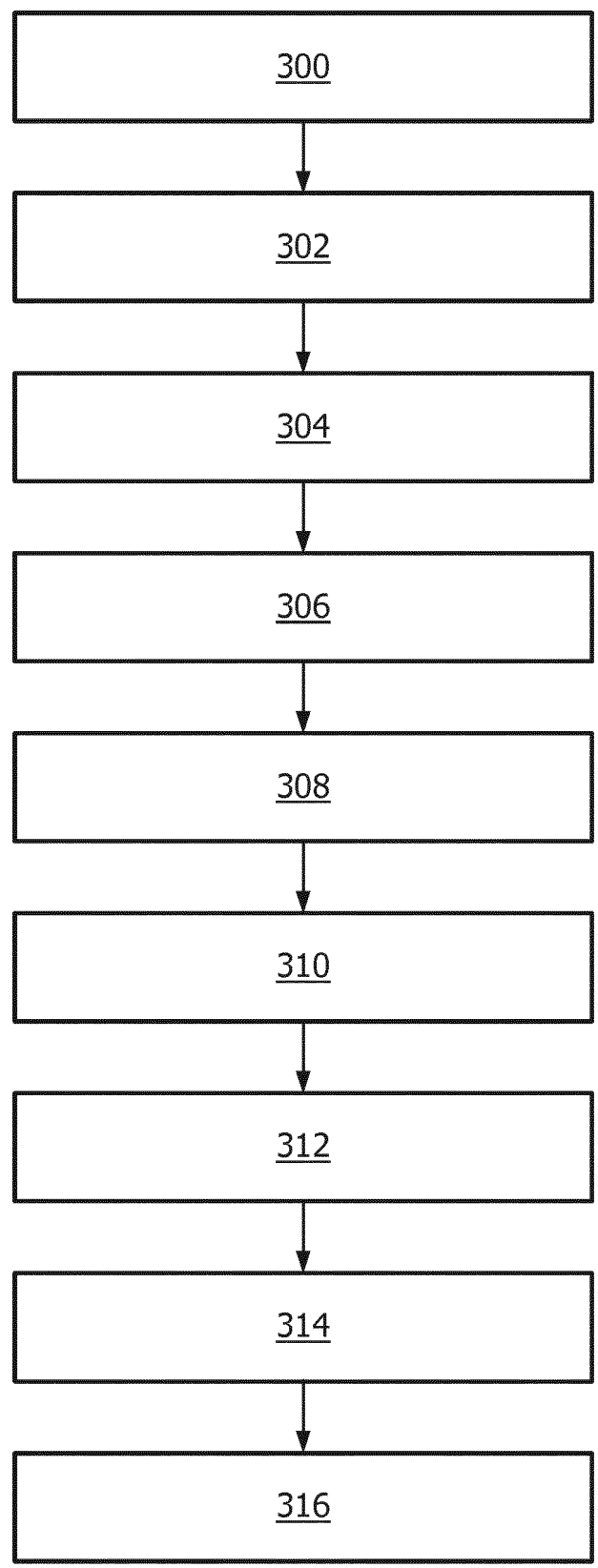
FIG. 3 shows a flow chart which illustrates a method of operating the magnetic resonance imaging system of FIG. 1 or FIG. 2.

FIG. 3 shows a flowchart which illustrates a method of operating the magnetic resonance imaging system 100 of FIG. 1 or the magnetic resonance imaging system 200 of FIG. 2. First in step 300 the magnetic resonance imaging system is controlled with the tagging pulse sequence commands 140 to acquire the tagged magnetic resonance data 144. Next in step 302 the magnetic resonance imaging system 100 or 200 is controlled with the control pulse sequence commands 142 to acquire the control magnetic resonance data 146. Next in step 304 a tagged magnitude image 148 is reconstructed from the tagged magnetic resonance data 144. Next in step 306 the control magnitude image 150 is reconstructed from the control magnetic resonance data 146. Next in step 308 the arterial image 152 or 152' is constructed by subtracting the tagged magnitude image 150 from the control magnitude image 148. Then in step 310 the arterial mask 154 is constructed using the arterial image 152 and identifying arteries in the arterial image 152. Next in step 312 the first phase image 156, the second phase image 158, and the third phase image 160 are reconstructed.

Optional steps may include step 314 where a first intermediate arterial phase contrast image 156' by setting voxels of the first phase image that are outside of the arterial mask 154 to a predetermined background value. Step 314 may also include constructing a second intermediate arterial phase contrast image 158' by setting voxels of the second phase image that are outside of the arterial mask 154 to a predetermined background value. Step 314 may further include constructing a third intermediate arterial phase contrast image 160' by setting voxels of the third phase image that are outside of the arterial mask 154 to a predetermined background value. Step 316 may include calculating a selective phase contrast arterial image 162 by adding the first intermediate arterial phase contrast image, the second intermediate arterial phase contrast image, the third intermediate arterial phase contrast image.

Examples may provide for a method for artery-selective, non-contrast-enhanced Magnetic Resonance Angiography is presented. It may be based on selective Arterial Spin Labeled (ASL) Magnetic Resonance Imaging to visualize a single artery of interest in conjunction with phase encoded information to visualize blood flow velocity and direction acquired in a single acquisition. The selective images obtained by Arterial Spin Labeling may be analyzed and processed using information of the phase encoded acquisitions. Extracting the information of both, selective ASL and phase-contrast information with different directional encoding from one acquisition leads to the final images, which display velocity, flow direction and morphology of a single selected artery. Furthermore, the venous system can be visualized as well.

The selective visualization of intracranial or other arteries arteries is an important differential diagnostic tool in radiological applications. Especially in neurovascular imaging, the information about a single selected artery (e.g. the carotid artery) can become crucial for an advanced diagnosis. Examples include intracranial cross-flow in patients with stenotic arteries, where the contralateral side supplies both hemispheres in part or in total. However, imaging all vessels at once would not suffice in finding this information. Another example are arterio-venous-malformations (AVM), as the identification of individual feeding arteries is crucial for the subsequent treatment planning Not only the identification and flow territories of selected arteries are of importance, but also hemodynamic properties, which include flow directions, identification of turbulent flow and display of blood flow velocity. Current gold standard methods, including X-Ray digital subtraction angiography (DSA), computed tomography angiography (CTA) and even magnetic resonance imaging (MRI) are currently limited in terms of delivering all the information in a timely manner and without exposing patients to any risk (e.g. ionizing radiation).

In MRI, the selective visualization of individual arteries can be achieved by applying pre-pulses using selective spatial saturation or selective arterial spin labeling (ASL) methods. ASL is based on the principle of subtracting two images; one is denoted as "control" (no inversion of blood spins) and the other as "label" (inversion of blood spins). Inversion of the magnetization of blood spins is achieved using dedicated RF pulses, which are applied during the inflow of blood. By subtracting these images, the static tissue cancels out. In selective methods, this is also the case for non-labeled arteries and only signal from the tagged artery is visible. ASL techniques make it possible to visualize vessel morphology and flow territories. Obtaining information about hemodynamics is also possible using time-resolved acquisitions; however, a quantification is limited. This is due to the fact that such acquisitions are limited in both spatial and temporal resolution in order to keep the measurement times to clinically acceptable durations.

Phase-contrast angiography (PCA) is a method which makes it possible to measure blood flow direction and velocity. The measurement and visualization of such parameters in only a single artery of interest is not possible. However, this is important, because in patients with cerebrovascular diseases the blood flow can be altered and an advanced diagnosis (e.g. intra-cranial crossflow) is impeded when all vessels are visualized at the same time. Furthermore, also venous flow is visualized in PCA measurements, potentially degrading image quality and reducing diagnostic confidence of the arterial vasculature.

Examples may enable the gathering of artery-selective information in conjunction with important hemodynamic parameters like blood flow direction and velocity in the cerebrovascular system in a single acquisition within a clinically acceptable scan time and by advanced analysis and processing of the acquired data.

At least two acquisitions are required by means of selective ASL and phase contrast angiography which prolong scan times significantly and make the measurements prone to subject motion. Additionally, arterial and venous signal can be separated in order to only visualize the arterial or the venous vasculature.

The gold standard method of obtaining selective angiograms is X-Ray digital subtraction angiography (DSA). This method relies on selectively placing an endovascular catheter through the iliac (or brachial) artery and injection of contrast agent. However, this method is invasive due to the need for placing an arterial access and the application of X-Rays and contrast agent. Other available image modalities such as computed tomography angiography (CTA) and contrast-enhanced MRA impede artery-selective imaging as these methods require the injection of exogenous contrast agents. After passing through the pulmonary arteries and then being ejected from the heart, the bolus traverses into the arteries ("arterial phase") where image acquisition is subsequently performed as fast as possible to catch the first pass arterial inflow and visualize the hemodynamic properties. In fast CE-MRA methods, after the first pass of contrast agent has entered the brain, the later arriving arterial blood is visualized simultaneously with the venous outflow, which might impede the assessment of the arterial vasculature. While non-contrast enhanced methods pose an attractive alternative to contrast agent injection, they usually cannot be performed artery-selectively. The most commonly used method in Neuro-MRA is TOF Angiography, where the inflow of unsaturated arterial blood is used to form an image of the intracranial arteries. This method, however, only allows for static visualization of all arteries for morphological assessment of the cerebrovasculature, yet no information about a single artery can be obtained. Furthermore, no hemodynamic properties can be visualized or quantified.

Hemodynamic information can be obtained by using PCA. Here, information about flow is gathered by the application of a phase encoding gradient along the flow direction(s) of the arterial spins. Depending on the blood flow velocity, the individual spins experience a phase shift, which can be used to draw conclusions on the direction and velocity of the blood flow. Another method for the acquisition of intracranial arteries is based on Arterial Spin Labeling (ASL). The basic principle of ASL Angiography is the inversion of arterial water spins in the up streaming blood of a single artery or of all arteries at once. After acquisition of an image with inversion (label) and an image without inversion (control), subsequent subtraction results in angiograms with high SNR, as the background signal is ideally cancelled out. Despite making it possible to use ASL for selective and time-resolved imaging, detailed information about blood flow velocity or blood flow direction is not available.

In some examples, selective ASL and PCA information are obtained in a single acquisition, thereby allowing for artery selective velocity and flow imaging. The following contrasts can be generated from one ASL-PCA measurement:

Structural brain images (unsubtracted label/control acquisitions)
Directional encoded blood flow images (PCA phase acquisitions)
Static non-selective angiographic images (PCA magnitude image)
Static angiograms of selected arteries (subtracted label/control acquisitions)
A selective phase-contrast angiogram after applying the generated image mask to the phase encoded images
An image of each artery with velocity information
A venous-only image after removing the arterial signal from the PCA images An example pulse sequence may comprise a 90° saturation module (WET) is used in order to saturate the static tissue signal. Then ASL labeling is performed for a defined amount of time (e.g. 1000*ms*). This time is chosen according to the blood flow velocity so that all vessels are filled with previously inverted blood at the time of image acquisition. Such information is accessible from previous measurements in literature. During readout (e.g. Gradient Echo) directional encoding is performed using phase encoding gradients. Phase encoding can be performed in one (e.g. right-left, feet-head, anterior-posterior) direction or more. This experiment is performed twice, to acquire complete label and control images as in conventional ASL approaches. A schematic of the sequence structure is displayed in FIGS. 4 and 5.

Figure 4:
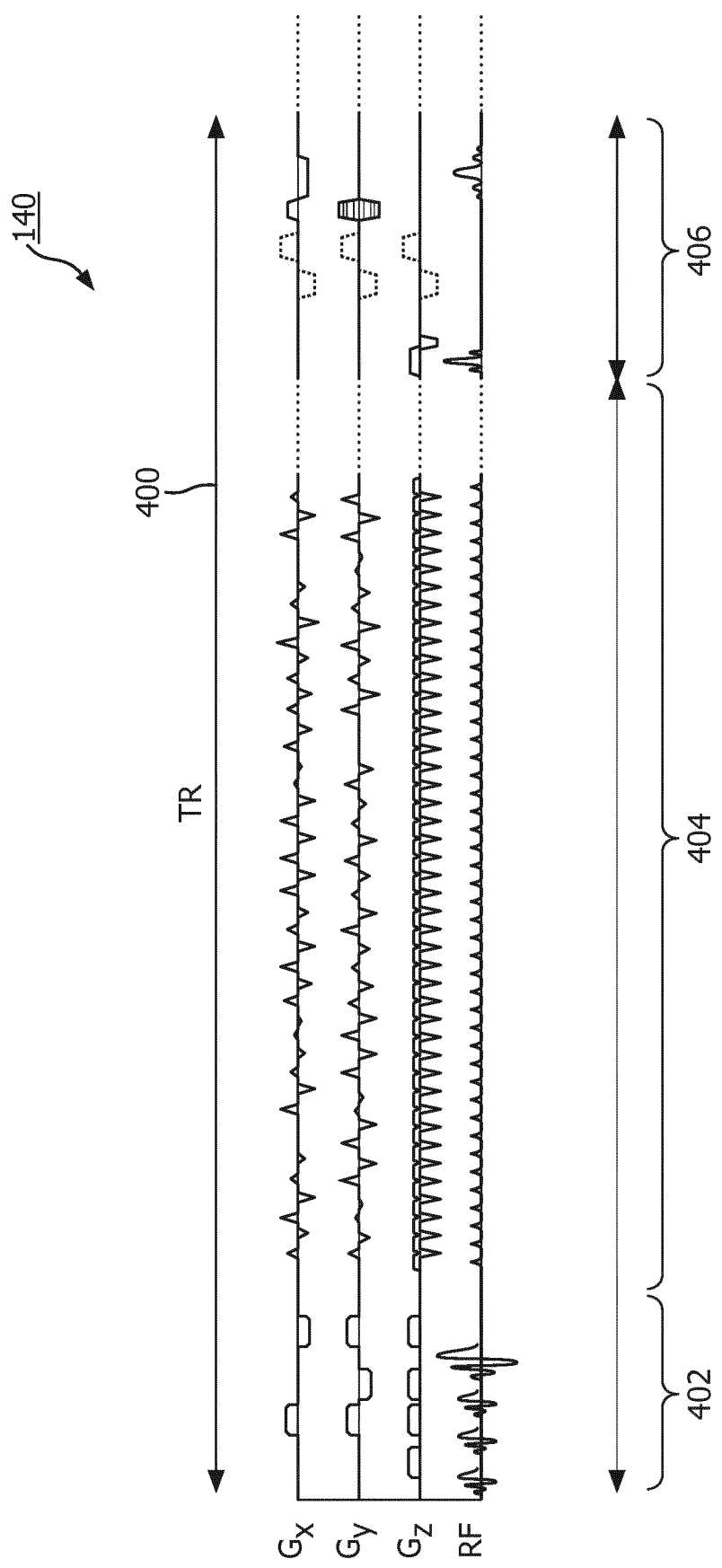
FIG. 4 shows a timing chart which illustrates one TR of tagging pulse sequence commands.

FIG. 4 is used to illustrate the tagging pulse sequence commands 140. FIG. 4 shows one TR or pulse repetition 400 of the tagging pulse sequence commands 140. The pulse repetition 400 comprises an optional pre-saturation portion 402, a tagging inversion pulse portion 404, and a phase-contrast readout 406. The pre-saturation portion 402 is not necessary but if it is used it may reduce the signal-to-noise and artefacts in the tagged magnitude image. The tagging inversion pulse portion 404 in this case is for selectively labeling a small volume and not for a plane. In FIG. 4, Selective labeling is realized using a selective ASL technique. In this approach, super-selective Arterial Spin Labeling is used. Readout is performed after sufficient filling of all arteries. The phase-encoding gradients are applied in one, two or in all three logical axes sequentially.

Figure 5:
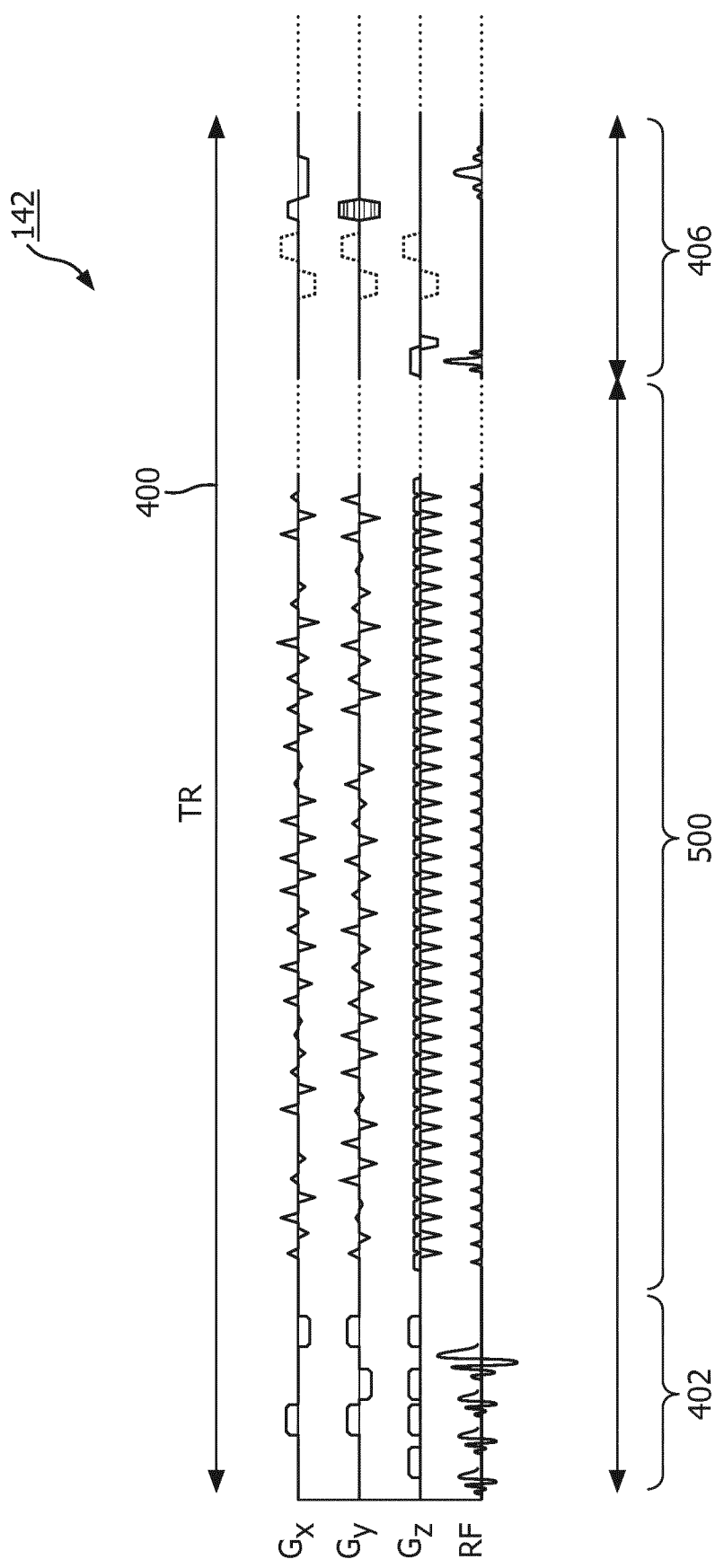
FIG. 5 shows a timing chart which illustrates one TR of control pulse sequence commands.

FIG. 5 shows an example of one pulse repetition 400 of a control pulse sequence command 142. The pulse repetition of FIG. 5 is similar to that of FIG. 140. It comprises the same preset optional pre-saturation portion 402, a control inversion pulse portion 500 and the same phase-contrast readout 406. The control inversion pulse portion 500 is similar to the tagging inversion pulse portion 404 except that the control inversion pulse portion 500 does not cause inversion within the tagging location. The control inversion pulse portion 500 may be chosen such that the magnetization transfer effect within the region of interest is essentially equivalent to the magnetization transfer effect caused by the tagging inversion pulse portion 404.

Post-processing of this data allows for artery-selective functional assessment of blood flow. From the ASL data, selective angiograms are generated using arithmetic image subtraction. From these angiograms, a binary mask is created, which is then applied to the three directional encoded images of the PCA dataset. Subsequent merging of these three images results in the final selective PCA images, presenting blood flow velocity in all phase encoding directions. A flow-chart of how image analysis and processing is performed is shown in FIGS. 6 and 7.

Figure 6:
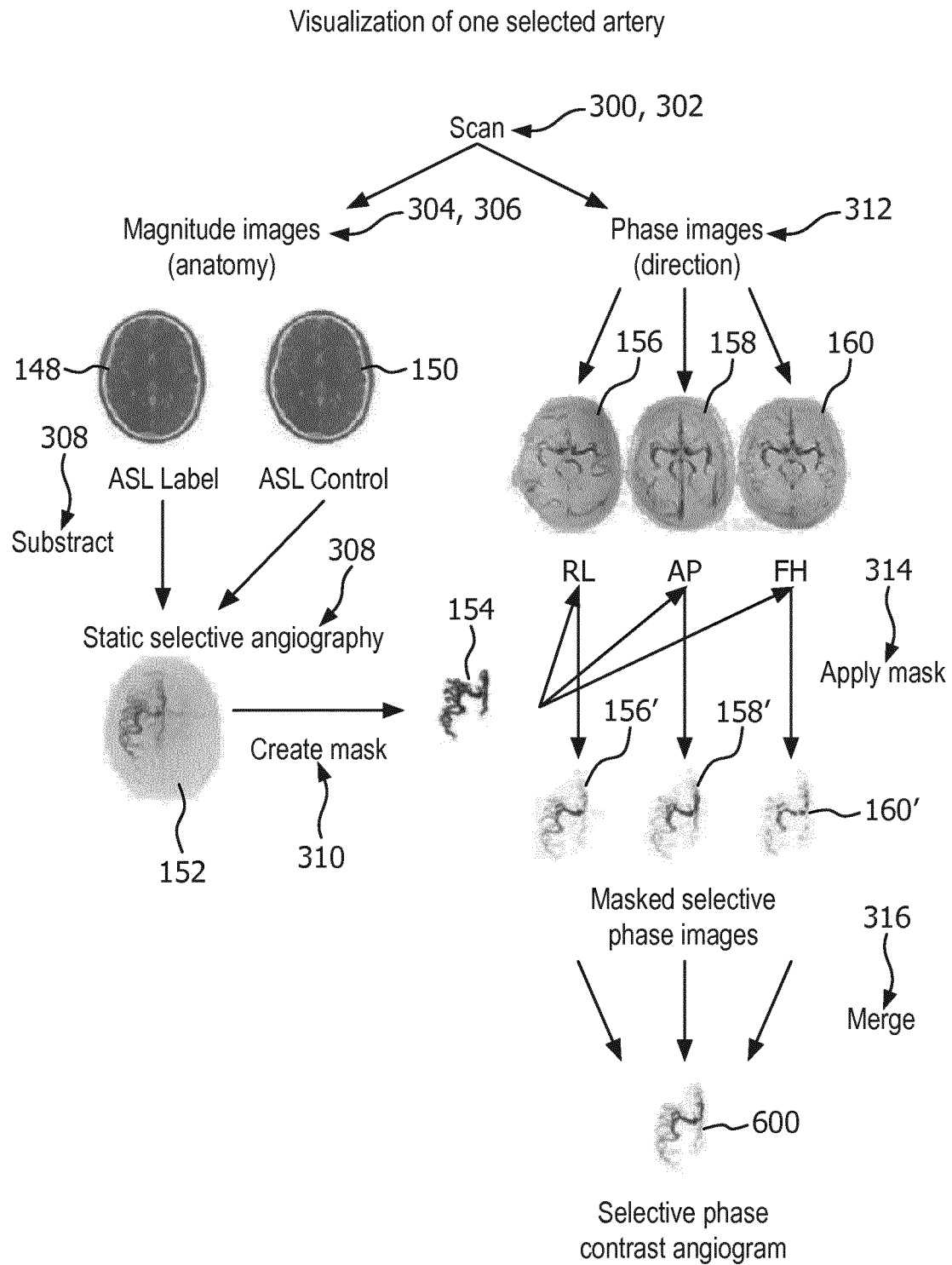
FIG. 6 shows a flow chart which illustrates a method of producing a selective phase contrast angiogram.

FIG. 6 shows a method of visualizing a single artery selectively and constructing an arterial image 152 for that artery and also for constructing a venous image 164 at the same time. After the tagged magnetic resonance data 144 and the control magnetic resonance data 146 have been acquired the tagged magnitude image 148 and the control magnitude image 150 are reconstructed. The labeled or tagged magnitude image 150 is then subtracted from the control magnitude image 148. This is used to calculate the arterial image 152. Then either by thresholding or using the more complicated segmentation technique the arterial mask 154 is calculated. The tagged magnetic resonance data or the control magnetic resonance data is then used to create three phase images in different directions. Shown are the first phase image 156, the second phase image 158 and the third phase image 160. The method may be formed in several different ways. For example the three phase images 156, 158, and 160 may first be combined and then the mask 154 may be applied. In the example shown in this FIG. the mask is applied independently to each of the three phase images first, 156, 158, 160. Image 156' is the masked version 156' of the first phase image 156. Image 158' is a masked version of the second phase image 158 and image 160' is a masked version of image 160. Only the voxels within the mask region 154 are taken. These three mask images which represent flow of blood in the three different directions may then be combined into a selected phase-contrast arterial image 600. For example different colors or other labels within the image 600 could be used to represent blood flow within the different directions.

FIG. 6 shows a flowchart displaying how image data analysis and processing is performed for the visualization of the right internal carotid artery. From the magnitude images, the static selective ASL angiography can be obtained. This image is then post-processed (binary mask creation) and applied to the non-selective phase-contrast images. A combination of all phase encoded directions results in the final images.

Figure 7:
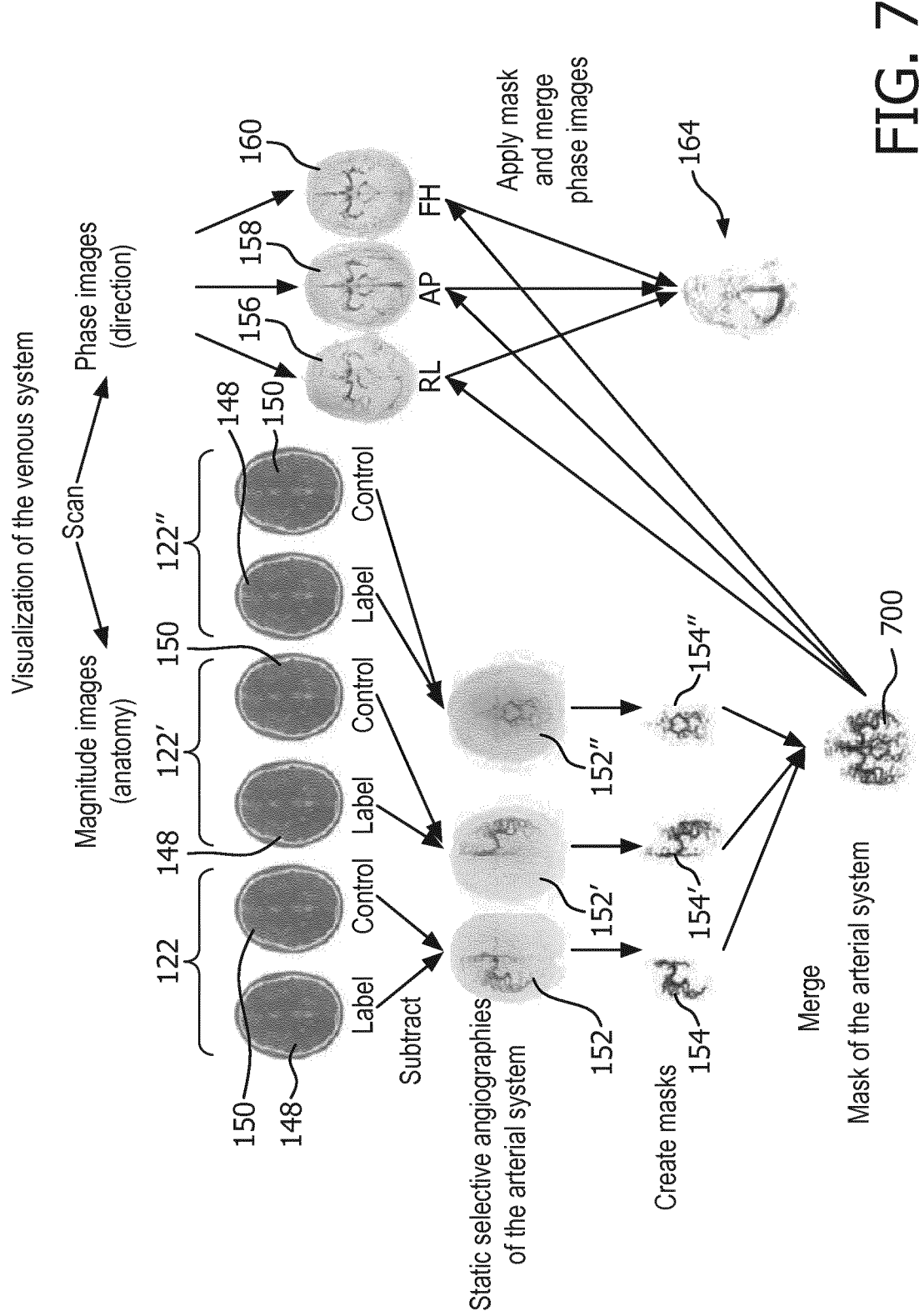
FIG. 7 shows a flow chart which illustrates a method of visualizing a venous system.

FIG. 7 illustrates how the venous system can be analyzed. In this example three different arteries are labeled selectively. They were labeled using the tagging volumes 122, 122' and 122". From each of the magnetic resonance data a control 150 and magnitude image 148 are reconstructed. From each pair of tagged magnitude image 148 and control magnitude image 150 an arterial image 152, 152' and 152" are calculated. Then from each of these arterial images a mask 154, 154', 154" is created. These may then be all merged into a composite arterial mask 700. As with FIG. 6, the three phase images 156, 158, 160 in the three different directions are reconstructed. Then the composite arterial mask 700 is applied to each of the phase images 156, 158 and 160. In this case voxels within the arterial mask in the corresponding phase images 156, 158, and 160 are set to a predetermined value such as zero. After the mask has been applied to each of the images 156, 158, 160, the three images are then merged or combined to form the venous image 164. The venous image 164 then shows a mapping of the flow of blood in different directions. For example a color coding system can be used to indicate the direction of blood flow within a three-dimensional image.

Figure 8:
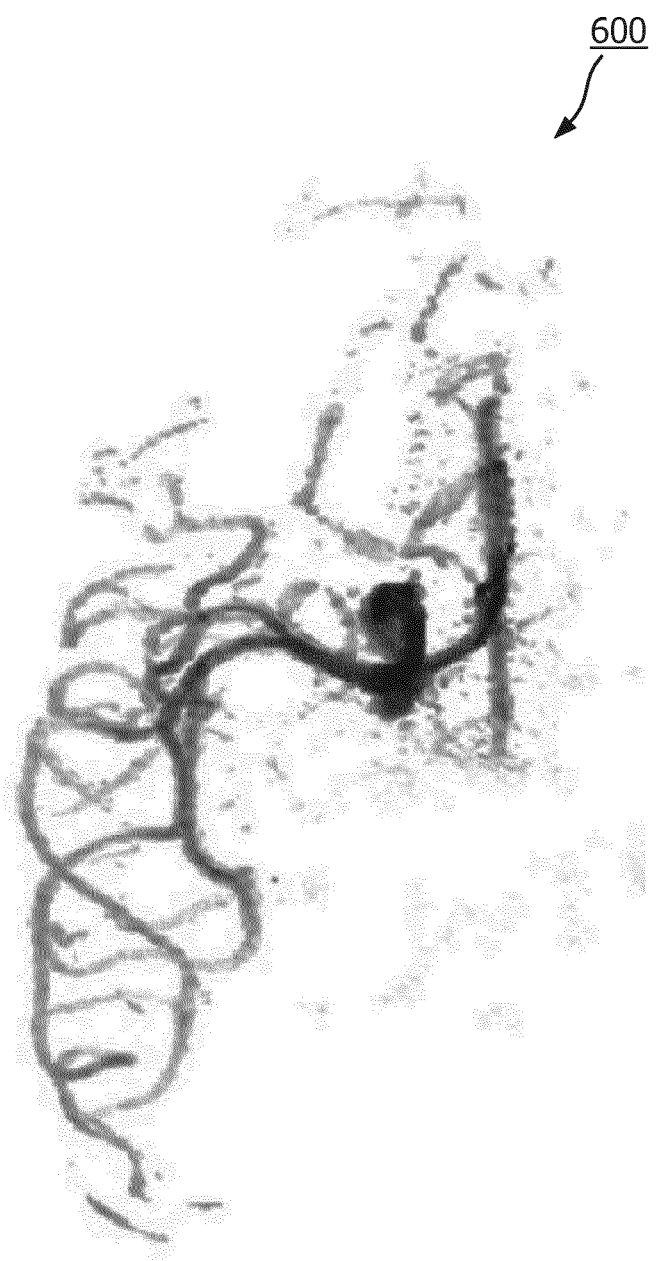
FIG. 8 illustrates an example of a mapping of the right interal carotid artery.

FIG. 8 displays how image analysis and processing is performed to only visualize the venous system. From the magnitude images of all selectively labelled arteries, the static selective ASL angiography images can be obtained. These images are then post-processed (binary mask creation) and put into one frame in order to generate a mask of the complete arterial vasculature. Subsequently, this mask is applied to the non-selective phase-contrast images in order to discriminate arterial and venous vessels. Finally, the individual phase encoded images (RL, AP, FH) presenting only venous information can be combined into one image. Obtainable Image Contrast:

Primarily, magnitude images for the evaluation of anatomical structures are readily available. Additionally, directional phase encoded images, usually performed in all three logical axis of the scanner coordinate system are available. These images are also used to visualize non-selective static angiography images.

Post-processing of the ASL data is performed as subtraction of the control and label images, so that static background signal and the non-labeled arteries are cancelled out, leaving only signal of the labeled artery. This is performed for each labeled artery. From these angiograms, a binary mask is created, which is applied to the three directional encoded images from the PCA data. To generate this mask, several techniques can be used. These include for example treshholding of the source images, the use of segmentation algorithms or discrimination by the measured velocity (i.e. fast velocities correspond to arteries, while slow velocities are identified as veins). Subsequent merging of these three masked images results in the final images, because all unwanted (contralateral and venous) vessel information is discarded after application of the image mask. The final images present velocity information and flow direction for individually selected arteries only. A flow-chart of how data analysis and processing are performed is shown in FIG. 6.

To acquire images of the venous system, the data analysis and processing is performed differently. Hence, the information about all cerebral arteries is needed as the localization of arteries can be used to indirectly obtain the location of the veins. For that purpose, all artery-selective images have to be combined into a single mask to display the whole arterial tree. Applying this information on the phase images, it is possible to visualize only venous flow. This flowchart is displayed in FIG. 7.

Image representation can be performed in several ways. For example, the directional information is presented in a single artery or the velocity information for each single artery is shown on a single image with individual colorbars representing velocity of each artery. These examples, without colorbars, are shown in FIGS. 8 and 9.

FIG. 8 shows an example of a selective phase-contrast arterial image 600. FIG. 8 is a projection of a three-dimensional image onto the paper or plane. FIG. 8 shows the directional mapping of the right internal carotid artery. The anterior posterior direction is displayed in red in the original three-dimensional image. The right left direction may be displayed in blue and the feet head flow direction may be displayed in green. However, color is not shown in the projection of FIG. 8.

Figure 9:
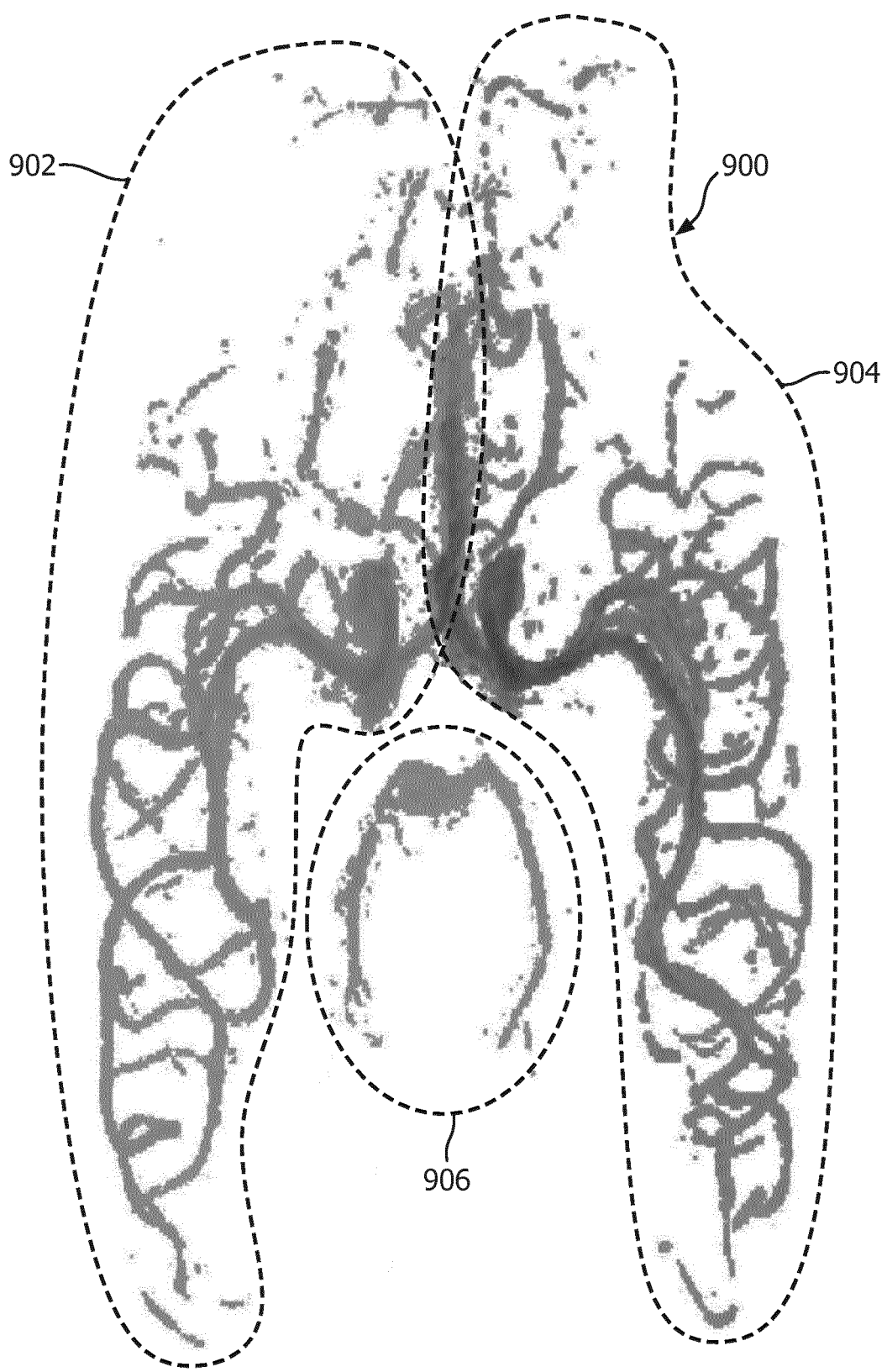
FIG. 9 illustrates a mapping of three arteries in a brain.

FIG. 9 shows a further example of a selective phase-contrast arterial image 900. In this example velocity mapping of three major brain feeding arteries in a healthy volunteer is displayed. The image shown in FIG. 9 is a projection of the three-dimensional image onto a plane. In the original three-dimensional image the right internal carotid artery is displayed in red, the left internal carotid artery is displayed in green and the posterior circulation is displayed in blue. The intensity of these different colors was scaled to show the velocity of blood through each of the arteries. This however is not displayed on FIG. 9. Dashed lines are used to indicate which portion of FIG. 9 belongs to the right internal carotid artery 902, the left internal carotid artery 904, and the posterior circulation 906. There is a region that overlaps both region 902 and 904 where some of the blood flow is due to the right internal carotid artery 902 and part of the blood flow is due to the left internal carotid artery 904. FIG. 9 illustrates a velocity mapping of the three major brain feeding arteries in a healthy volunteer. The right internal carotid artery is displayed in red, the left in green and the posterior circulation in blue. The intensity is scaled according to the blood flow velocities.

Applications include cerebrovascular diseases with complex and diffuse flow patterns, for which not only the selective information about an artery is important, but also underlying hemodynamic properties. These are especially arterio-venous malformations (AVM), but also fistulas, and tumor feeding arteries. Other applications include stenotic arteries, potentially leading to stroke.

Venous diseases can also be visualized separately by this method, as the information can be extracted from the data using the pre-processed arterial information. Here, applications could include venous stenosis (e.g. in pseudo-tumor cerebri patients) or thrombosis in the sinus veins.

Examples are not necessarily limited to the cerebral vasculature, but might also be used to visualize other arteries. These include selective visualization of the renal arteries, the coronary arteries, as well as the peripheral lower leg arteries.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
122 tagging location
126 computer system
128 hardware interface
130 processor
132 user interface
134 computer storage
136 computer memory
140 tagging pulse sequence commands
142 control pulse sequence commands
144 tagged magnetic resonance data
146 control magnetic resonance data
148 tagged magnitude image
150 control magnitude image
152 arterial image
154 arterial mask
156 first phase image
156' first intermediate arterial phase contrast image
158 second phase image
158' second intermediate arterial phase contrast image
160 third phase image
160' third intermediate arterial phase contrast image
162 selective phase contrast arterial image
162' selective phase contrast arterial image
164 venous image
166 composite image
170 machine executable instructions
200 magnetic resonance imaging system
300 acquire tagged magnetic resonance data by controlling the magnetic resonance imaging system with the tagging pulse sequence commands
302 acquire control magnetic resonance data by controlling the magnetic resonance imaging system with the control pulse sequence commands
304 reconstruct a tagged magnitude image using the tagged magnetic resonance data
306 reconstruct a control magnitude image using the control magnetic resonance data
308 construct an arterial image by subtracting the tagged magnitude image from the control magnitude image
310 construct an arterial mask using the arterial image by identifying arteries in the arterial image
312 reconstruct a first phase image, a second phase image, and a third phase image using either the tagged magnetic resonance data and/or the control magnetic resonance data, wherein the first phase image is reconstructed using using phase encoding in the first direction, wherein the second phase image is reconstructed using phase encoding in the second direction;
314 construct a first intermediate arterial phase contrast image, a second intermediate arterial phase contrast image, and a third intermediate arterial phase contrast image by setting voxels of the first phase image, the second phase image, and the that are outside of the arterial mask to a predetermined background value
316 calculate a selective phase contrast arterial image by adding the first intermediate arterial phase contrast image, the second intermediate arterial phase contrast image, the third intermediate arterial phase contrast image 400 pulse repetition
402 presaturation portion
404 tagging inversion pulse portion
406 phase contrast readout
500 control inversion pulse portion
600 selective phase contrast angiogram
700 composite arterial mask
900 selective phase contrast angiogram
902 blood flow in right internal carotid artery
904 blood flow in left internal carotid artery
906 blood flow in posterior circulation

The invention claimed is:

1. A magnetic resonance imaging system for imaging a subject, wherein the magnetic resonance imaging system comprises:
    a memory for storing machine executable instructions; and
    a processor configured to execute the machine-readable instructions to control the magnetic resonance imaging system to:
        acquire tagged magnetic resonance data by controlling the magnetic resonance imaging system to apply a tagging inversion pulse to spin label a tagging location within the subject followed by a phase-contrast readout with phase-contrast encoding in at least one direction;
        acquire control magnetic resonance data by controlling the magnetic resonance imaging system to apply a control inversion pulse followed by the phase-contrast readout with the phase-contrast encoding in the at least one direction;
        reconstruct a tagged magnitude image using the tagged magnetic resonance data;
        reconstruct a control magnitude image using the control magnetic resonance data;
        construct an arterial image by subtractively combining the control magnitude image and the tagged magnitude image; and
        reconstruct a phase image using either the tagged magnetic resonance data and/or the control magnetic resonance data at least partially using the phase-contrast encoding in the at least one direction, wherein the phase image is configured to be used for detecting blood flow.

2. The magnetic resonance imaging system of claim 1, wherein execution of the machine executable instructions causes the processor to construct an arterial mask using the arterial image by identifying arteries in the arterial image.

3. The magnetic resonance imaging system of claim 2, wherein the arterial mask is created using the arterial image according to any one of the following:
    by thresholding the arterial image using a predetermined threshold value, wherein portions of the arterial image above the predetermined threshold value are identified as being arterial regions;
    by segmenting the arterial image;
    by applying an anatomical atlas to the arterial image;
    by fitting a deformable shape model to the arterial image; and
    by combinations thereof.

4. The magnetic resonance imaging system of claim 2, wherein execution of the machine executable instructions further causes the processor to construct a selective phase contrast arterial image at least partially by setting voxels of the phase image that are outside of the arterial mask to a predetermined background value.

5. The magnetic resonance imaging system of claim 2, wherein execution of the machine executable instructions further cause the processor to construct a venous image at least partially by setting voxels within the venous image that are within the arterial mask to a predetermined background value.

6. The magnetic resonance imaging system of claim 5, wherein execution of the machine executable instructions cause the processor to calculate a composite image by combining the arterial image and the venous image into a composite image.

7. The magnetic resonance imaging system of claim 1, further including:
    performing presaturation before the tagging inversion pulse, and performing presaturation before the control inversion pulse.

8. The magnetic resonance imaging system of claim 1, wherein the tagging location is selective for a single artery.

9. The magnetic resonance imaging system of claim 8, wherein execution of the machine executable instructions cause the processor to:
    repeatedly acquire the tagged magnetic resonance data and the control magnetic resonance data for a predetermined number of tagging volumes, and
    calculate the arterial image for each of the predetermined number of tagging volumes.

10. The magnetic resonance imaging system of claim 1, wherein the tagging location is non-selective.

11. The magnetic resonance imaging system of claim 1, wherein execution of the machine executable instructions further causes the processor to receive the tagging location.

12. The magnetic resonance imaging system of claim 11, wherein execution of the machine executable instructions further cause the processor to receive the tagging location by segmenting a preliminary medical image.

13. The magnetic resonance imaging system of claim 1, wherein acquiring the tagged magnetic resonance data includes magnetization transfer, and acquiring the control magnetic resonance data includes magnetization transfer, and wherein the subtractively combining of the control and tagged magnitude images cancels out an effect of the magnetization transfer in the arterial image.

14. A non-transitory computer program product carrying machine executable instructions for execution by a processor controlling a magnetic resonance imaging system for imaging a subject, wherein execution of the machine executable instructions causes the processor to:
    acquire tagged magnetic resonance data by controlling the magnetic resonance imaging system with a tagging pulse sequence, wherein the tagging pulse sequence comprises a tagging inversion pulse for spin labeling a tagging location within the subject and a phase-contrast readout portion, wherein the phase-contrast readout portion comprises phase-contrast encoding in at least one direction configured to visualize blood flow velocity and direction;
    acquire control magnetic resonance data by controlling the magnetic resonance imaging system with a control pulse sequence, wherein the control pulse sequence comprises a control inversion pulse and the phase-contrast readout portion with the phase-contrast encoding in at least one direction;
    reconstruct a tagged magnitude image using the tagged magnetic resonance data;
    reconstruct a control magnitude image using the control magnetic resonance data;

construct an arterial image by subtracting the control magnitude image and the tagged magnitude image; and reconstruct a phase image using either the tagged magnetic resonance data and/or the control magnetic resonance data at least partially using phase encoding in the at least one direction, wherein the phase image is configured to be used for detecting blood flow.

15. A method of operating a magnetic resonance imaging system for imaging a subject, wherein the method comprising:

acquiring tagged magnetic resonance data by controlling the magnetic resonance imaging system with a tagging inversion pulse for spin labeling a tagging location within the subject and a phase-contrast readout including phase-contrast encoding in at least one direction configured to visualize blood flow velocity and direction;

acquiring control magnetic resonance data by controlling the magnetic resonance imaging system with a control inversion pulse sequence followed by the phase-contrast readout;

reconstructing a tagged magnitude image using the tagged magnetic resonance data;

reconstructing a control magnitude image using the control magnetic resonance data;

constructing an arterial image by subtracting the control magnitude image and the tagged magnitude image; and reconstructing a phase image using either the tagged magnetic resonance data and/or the control magnetic resonance data, wherein the phase image is at least partially reconstructed using the phase-contrast encoding in the at least one direction, wherein the phase image is configured to be used for detecting blood flow.

16. A magnetic resonance imaging system for imaging a subject, wherein the magnetic resonance imaging system comprises:

a memory for storing machine executable instructions for (i) a tagging pulse sequence, and for (ii) a pulse control sequence, the tagging pulse sequence including a tagging inversion pulse for spin labeling a tagging location within the subject followed by a phase-contrast readout including phase-contrast encoding in at least one direction, configured to visualized blood flow velocity and direction, the control pulse sequence including a control inversion pulse and a phase-contrast readout including phase-contrast encoding in at least one direction configured to visualized blood flow velocity and direction; and a processor for controlling the magnetic resonance imaging system, wherein execution of the machine executable instructions causes the processor to:

acquire tagged magnetic resonance data by controlling the magnetic resonance imaging system with the tagging pulse sequence;

acquire control magnetic resonance data by controlling the magnetic resonance imaging system with the control pulse sequence;

reconstruct a tagged magnitude image using the tagged magnetic resonance data;

reconstruct a control magnitude image using the control magnetic resonance data;

construct an arterial image by subtractively combining the control magnitude image and the tagged magnitude image; and reconstruct a phase image using at least one of the tagged magnetic resonance data and/or the control magnetic resonance data at least partially using phase-contrast encoding in the at least one direction, wherein the phase image is configured to be used for detecting blood flow.

17. The method of claim 15, further including constructing an arterial mask using the arterial image and identifying arteries in the arterial image.

18. The method of claim 17, further including constructing a venous image including setting voxels within the venous image that are within the arterial mask to a predetermined background value.

19. The method of claim 17, wherein the tagging location is selected for a single artery.

20. The method of claim 19, further including:

repeatedly acquiring tagged magnetic resonance data and control magnetic resonance data for a plurality of tagging volumes, and calculate the arterial image for each of the tagging volumes.

* * * * *